(12) United States Patent
Urdea et al.

(10) Patent No.: US 8,232,065 B2
(45) Date of Patent: Jul. 31, 2012

(54) SYSTEMS AND METHODS FOR DEVELOPING DIAGNOSTIC TESTS BASED ON BIOMARKER INFORMATION FROM LEGACY CLINICAL SAMPLE SETS

(75) Inventors: Michael S. Urdea, Alamo, CA (US); Michael P. McKenna, Oakland, CA (US)

(73) Assignee: Tethys Bioscience, Inc., Emeryville, CA (US)

( * ) Notice: Subject to any disclaimer, the term of this patent is extended or adjusted under 35 U.S.C. 154(b) by 691 days.

(21) Appl. No.: 12/300,019

(22) PCT Filed: May 8, 2007

(86) PCT No.: PCT/US2007/011196
§ 371 (c)(1),
(2), (4) Date: Jun. 29, 2009

(87) PCT Pub. No.: WO2007/133586
PCT Pub. Date: Nov. 22, 2007

(65) Prior Publication Data
US 2011/0098187 A1    Apr. 28, 2011

Related U.S. Application Data

(60) Provisional application No. 60/798,867, filed on May 8, 2006.

(51) Int. Cl.
*G01N 31/00* (2006.01)
*G01N 33/53* (2006.01)

(52) U.S. Cl. ........ 435/7.21; 435/7.1; 436/501; 436/518; 424/9.1; 424/520; 422/50; 530/300; 530/350

(58) Field of Classification Search .................. None
See application file for complete search history.

(56) References Cited

U.S. PATENT DOCUMENTS

| | | |
|---|---|---|
| 6,592,822 B1 | 7/2003 | Chandler |
| 7,572,640 B2 | 8/2009 | Goix et al. |
| 7,723,050 B2 | 5/2010 | Urdea et al. |
| 8,119,358 B2 | 2/2012 | Urdea et al. |
| 2004/0175695 A1 | 9/2004 | Debad et al. |
| 2005/0079099 A1 | 4/2005 | Spain et al. |
| 2006/0078998 A1 | 4/2006 | Puskas et al. |
| 2007/0218519 A1 | 9/2007 | Urdea et al. |
| 2007/0259377 A1 | 11/2007 | Urdea et al. |
| 2008/0003685 A1 | 1/2008 | Goix et al. |
| 2008/0064113 A1 | 3/2008 | Goix et al. |
| 2008/0158543 A1 | 7/2008 | Puskas et al. |
| 2008/0171319 A1 | 7/2008 | Urdea et al. |
| 2008/0171352 A1 | 7/2008 | Goix et al. |
| 2009/0171590 A1 | 7/2009 | Puskas et al. |
| 2009/0239253 A1 | 9/2009 | Watkins |
| 2009/0263400 A1 | 10/2009 | Urdea et al. |
| 2010/0197028 A1 | 8/2010 | Watkins et al. |
| 2010/0329929 A1 | 12/2010 | Goix et al. |
| 2011/0008805 A1 | 1/2011 | Urdea et al. |

FOREIGN PATENT DOCUMENTS

| | | |
|---|---|---|
| WO | WO-2006/036182 A2 | 4/2006 |
| WO | WO-2011/059720 A2 | 5/2011 |
| WO | WO-2011/059721 A1 | 5/2011 |

OTHER PUBLICATIONS

Anderson et al., The human plasma proteome: A nonredundant list developed by combination of four separate sources. *Molec. Cell Proteomics*, 3.4: 311-26 (2004).
Anderson et al., The human plasma proteome: History, character, and diagnostic prospects, *Molec. Cell Proteomics*, 1.11: 845-67 (2002).
Anderson, A list of candidate cancer biomarkers for targeted proteomics, *Biomarker Insights*, 2: 1-48 (2006).
Anderson, Candidate-based proteomics in the search for biomarkers of cardiovascular disease, *J. Physiol.*, 563 (1): 23-60 (2005).
European Search Report, European Application No. 11185326.3, dated Nov. 21, 2011.
Ginsburg et al., Translating genomic biomarkers into clinically useful diagnostics. *Expert Rev. Mol. Diagn.*, 6(2): 179-91 (2006).
ID Serology, <<http://web.archive.org/web/20040207020824/www.rulesbasedmedicine.com/MAPS/human.asp>>, dated Feb. 7, 2004.
International Search Report, PCT/US2007/01196, United States Patent and Trademark Office, dated Nov. 16, 2007.
Singulex Publications, <<http://www.singulex.com/literature.html>, dated Jan. 1, 2006.
Sullivan et al., Phases of biomarkers development for early detection of cancer. *J. Natl. Cancer Inst.*, 93(14): 1054-61 (2001).
Supplementary European Search Report, European Application No. 07776917.2, dated May 11, 2009.
The big picture from a small sample at low cost. <<http://web.archive.org/web/20040730032517/http://www.rulesbasedmedicine.com/>>, dated Jul. 30, 2004. Wu et al., Development and preliminary clinical validation of a high sensitivity assay for cardiac troponin using a capillary flow (single-molecule) fluorescence detector. <<http://www.singulex.com/documents/Singulex_Troponin_poster.pdf>>, dated Jan. 1, 1996.
U.S. Appl. No. 11/784,186, Goix et al.
U.S. Appl. No. 12/060,997, Goix et al.
U.S. Appl. No. 60/636,158, Puskas.
U.S. Appl. No. 60/624,158, Puskas.
U.S. Appl. No. 60/613,881, Puskas.

*Primary Examiner* — Lisa Cook
(74) *Attorney, Agent, or Firm* — Marshall, Gerstein & Borun LLP

(57) ABSTRACT

Disclosed are systems and methods for developing diagnostic tests (e.g., detection, screening, monitoring, and prognostic tests) based on biomarker information from legacy clinical sample sets, for which only small sample volumes (e.g., about 0.05 to about 1.0 mL or less per sample) are typically available. For example, biomarkers (e.g., about 10, 50, 100, 150, 200, 300, or more) may be detected in the clinical samples through the use of single molecule detection and each biomarker may be detected in an assay that includes about 1 μL or less of a legacy clinical sample.

15 Claims, 7 Drawing Sheets

| Company | Product | Technology Description | Detection Limit (Molecules) | CV |
|---|---|---|---|---|
| Ciphergen | System 4000 | SELDI Mass Spectrometry | 6.0E+11 | 20% |
| ForteBio | Octet | Bio-layer interferometry | 1.9E+08 | 15% |
| Luminex | 100 IS | Coded bead and flow detection system | 7.2E+05 | 10% |
| Meso-scale | Sector | Electro Chemiluminescence | 1.3E+06 | 10% |
| Singulex | Erenna | Single molecule fluorescent detection | 1.0E+05 | 10% |
| US Genomics | Trilogy 2020 | Single molecule fluorescent detection | 2.0E+04 | 10% |
| Zeptosens | ZeptoReader | Planar wave guide array detection | 1.7E+06 | 15% |

Fig. 7

SYSTEMS AND METHODS FOR DEVELOPING DIAGNOSTIC TESTS BASED ON BIOMARKER INFORMATION FROM LEGACY CLINICAL SAMPLE SETS

CROSS-REFERENCE TO RELATED APPLICATION

This application is a national phase filing under 35 U.S.C. 371 of PCT Application No. PCT/US2007/011196, filed May 8, 2007, which claims priority to U.S. Provisional Patent Application No. 60/798,867, filed May 8, 2006, both of which are incorporated by reference herein in their entirety.

FIELD OF THE INVENTION

Embodiments of the present invention relate to systems and methods for developing diagnostic tests and, more specifically, to systems and methods for developing diagnostic tests based on biomarker information from legacy clinical sample sets, for which only small sample sizes (e.g., about 0.05 to 1.0 mL per sample) are typically available. In a preferred embodiment, the biomarker information is detected in the clinical samples through the use of single molecule detection.

BACKGROUND OF THE INVENTION

Diagnostic tests have been provided for detecting, screening, monitoring, and/or predicting the future development of various health states (e.g., disease states) in a subject. Typically, the detecting, screening, monitoring, or prognosis is provided by a diagnostic test based, at least in part, on the level(s) of one or more biological markers ("biomarkers") in a clinical sample taken from the subject (e.g., the subject's blood), or the presence thereof. Such biomarkers are selected because the presence, absences, or levels of such biomarkers alone or in combination are indicative of the presence, stage, or future clinical course of the health state. Often times, but not necessarily, the diagnostic test may additionally be based on clinical information concerning the subject. Determining an appropriate diagnosis or prognosis for a subject can, for example, advantageously increase the subject's chances for survival and/or recovery.

Diagnostic tests must undergo a development stage during which the tests are formulated (and optionally tested/validated) using previously collected samples stored for future research and development needs. This process is prior to their use in diagnosing or predicting the development of disease in subjects in real time. The information used to formulate and validate the tests typically comes from clinical samples for a cohort of subjects for whom at least some biochemical and clinical data is known regarding the presence or absence of the health state under consideration. Thus, traditionally a party who is desirous of developing a diagnostic test for a given health state is required to commit significant resources to the collection of clinical samples (and optionally clinical information such as medical history) from subjects who have, and/or lack, the health state, often at various stages. This data collection process can take many years, depending on the type of disease being considered and the party's relative access to suitable subjects.

Traditional approaches for developing diagnostic tests also require the clinical samples that are collected to have sufficiently large volumes, and such large samples cannot always be readily obtained. Specifically, traditional biomolecular detection approaches require large sample volumes in order to allow for the selection of a set of biomarkers that will be useful in the determination of a patient's health state. Of all the biomarkers that are evaluated (e.g., 1-3, 150-300 biomarkers, or 1000 or more), only those biomarkers that are determined to aid in the determination of the health state in a patient are included in the final diagnostic test. For example, according to one approach, single-biomarker multiple ELISAs used to measure the presence or level of 300 biomarkers typically require a serum or plasma sample size of about 30 mL of specimen per individual (i.e., 100 uL per assay times 300 biomarkers). The required sample volume becomes 90 mL of specimen per individual if the assays are done in triplicate. This is a very large volume and is very impractical. In addition, few studies have ever been conducted where so much clinical sample was collected. Multiplexing, which involves measuring multiple biomarkers in the same reaction vessel, can reduce the overall required sample volume by way of conservation but requires compatibility between all the assay components and typically compromises sensitivity through increased background effects. As a result, on an assay by assay basis, individual assays are typically 10 or more fold more sensitive than their counterpart within a multiplexed assay.

In view of the foregoing, it would be desirable to provide systems and methods for developing diagnostic tests in which access to suitable clinical samples is improved and which rely on smaller sample volumes.

SUMMARY OF THE INVENTION

The above and other objects and advantages of the present invention are provided in accordance with the principles of the present invention described herein. Embodiments of the present invention relate to systems and methods for developing diagnostic tests based on biomarker information from legacy clinical sample sets, for which only small sample volumes (e.g., about 0.05 to 1.0 mL per individual) are typically available. As used herein, a "legacy clinical sample set" is one or more clinical samples (e.g., 10 to 5000 samples or more) collected in the past (i.e., retrospective sample collections). The use of legacy clinical samples, as opposed to performing the process of collecting clinical samples prospectively, reduces the resources and time that must be committed to developing new diagnostic tests. Legacy clinical samples may be from, for example, one or more past studies that occurred over a span of 1 to 40 years or more, which studies may be accompanied by tens to thousands of clinical parameters, traditional laboratory measurements that are considered risk factors or that provide additive information to enable a better clinical decision to be made, and other previously measured information (e.g., clinical data such as the subject's age, weight, ethnicity, medical history, and/or other information). In most cases, the legacy clinical samples are serum or plasma samples that have been stored for years at −80 degrees Centigrade or −20 degrees Centigrade. In other examples, a legacy clinical sample can include, for example, blood cells, ascites fluid, interstitial fluid, bone marrow, sputum, urine, or other biological sample. Examples of such past studies, which are included for the purpose of illustration and not limitation, are listed below:

1. DPP (Diabetes Prevention Program)—An NIH sponsored trail that studied the impact of lifestyle modifications, metformin vs. placebo. This study had 2.8 years follow-up with diabetes outcomes.
2. IRAS (Insulin Resistance Atherosclerosis Study)—Studied the impact of insulin resistance on the development of cardiovascular disease.

3. ARIC (Atherosclerosis Risk in Communities Study)—This study includes CVD and cardiovascular outcomes.
4. Finnish Diabetes Prevention Study—studied the impact of lifestyle changes on the development of diabetes.
5. Israeli Diabetes Research Group (MELANY)—Studied the development of diabetes in healthy normal subjects from the Israeli military
6. HDDRISC (Heart Disease and Diabetes Risk Indicators in a Screened Cohort)—collection of diabetes and cardiovascular outcomes.
7. WSCOPS (West of Scotland Coronary Prevention Study)—studied the impact of pravastatin on reduction of LDL and reduction in myocardial events
8. ASCOT (Anglo-Scandinavian Cardiac Outcomes Trial)—studied the impact of different medicines for lowering blood pressure and cholesterol. CVD outcomes collected.
9. SOF (Study of Osteoporotic Fractures)—Study looks for predictors of fracture in women over 65 years of age
10. NORA (National Osteoporosis Risk Assessment)—Studied fracture outcomes in women with varying BMD levels.
11. Framingham Heart Study—Related to identifying the common factors or characteristics that contribute to CVD by following its development over a long period of time in a large group of participants who had not yet developed overt symptoms of CVD or suffered a heart attack or stroke.
12. CARDIA—(Coronary Artery Risk Development in Young Adults) A longitudinal study designed to trace the development of risk factors for coronary heart disease in a cohort of 18-30 year olds (1985) in four U.S. cities.
13. Reykjavik Study—A long-term prospective population-based cardiovascular study of 33-79 year olds with 4 to 20 year follow-up (1967-91), in Iceland.
14. Malmo Preventive Project—A prospective, population-based study of the effects of interventions on mortality and cardiovascular morbidity in 32-51 year olds (1974-1992) in Sweden
15. Heart Protection Study—A very large, prospective, double-blind, randomized, controlled trial investigating prolonged use (>5 years) of a statin and an antioxidant vitamin cocktail in individuals 40 to 80 years old in the United Kingdom who had an elevated risk for CHD.
16. 4S (Scandinavian Simvastatin Survival Study)—Large double-blind, randomized trial designed to evaluate the effect of a statin on mortality and morbidity in patients with coronary heart disease (CHD).
17. DREAM (Diabetes Reduction Assessment with ramipril and rosiglitazone Medication) Study—A large, double-blind, placebo-controlled trial evaluating the effects of an ACE inhibitor and/or a thiazolidinedione on the development of diabetes, death, or regression to normoglycaemia in adults aged 30 years or more with impaired fasting glucose and/or impaired glucose tolerance, and no previous cardiovascular disease.
18. Physician's Health Study—a large cohort of apparently healthy male U.S. physicians aged 40 to 84 years in 1982, followed prospectively for an average of 60.2 months
19. WHI (Women's Health Initiative)—A very large, prospective study, involving both clinical trial and observational components, of women 50 to 79 years of age in the U.S., and is designed to examine the relationship between health, lifestyle, and risk factors for a variety of specific diseases, including CHD
20. WHS (Women's Health Study) A very large, double-blind, randomized, placebo-controlled trial to evaluate the effects of vitamin E and low-dose aspirin on cardiovascular disease and cancer in apparently healthy U.S. women, age 45 and older, which also included an observational extension
21. NHS (Nurses' Health Study)—A very large, prospective cohort study of nurses aged 30-55 (in 1976) designed to assess the long term effects of oral contraceptive use
22. NHS II (Nurses' Health Study II)—A very large, prospective cohort study of nurses aged 25-42 (in 1989) designed to assess the long term effects of oral contraceptives, diet and lifestyle risks.

In an embodiment of the present invention, methods and systems are provided for developing a diagnostic test for determining a health state in a patient (e.g., a test for a predicting or diagnosing disease such as diabetes, osteoporosis, pre-osteoporosis, or any other disease), in which at least one biomarker is detected in at least one legacy clinical sample. For example, the biomarker may be detected in an immunoassay that includes about 1 uL or less of the legacy clinical sample. The detection may be performed by, for example, a single molecule detector. Typically, although not necessarily, developing a new diagnostic test comprises detecting multiple biomarkers from multiple clinical samples, including samples from subjects known have a given health state, or with respect to reference ranges from a known normal population. The detected biomarker(s) are then analyzed for an association with the health state. For example, a statistical analysis may be performed to determine whether the biomarker statistically correlates with the presence or absence of the health state, or alternatively correlates with the existing gold standard (whether biomarker, clinical parameter, or otherwise) used for defining the presence of the health state (for example, fasting glucose level for diabetes, blood pressure for hypertension as a health state, or coronary imaging scores or percentage occlusions/stenosis for coronary artery disease). Alternatively or additionally, the analysis may involve determining whether the inclusion of the biomarker in a formula or machine learning analysis increases an ability of a mathematical function resulting from the machine learning analysis to determine the health state in a patient.

In another embodiment, clinical parameters (e.g., age, weight, ethnicity, medical history, and/or other clinical information) that accompany the legacy clinical sample(s) may also be analyzed for an association with the health state.

In yet another embodiment, methods and systems are provided for developing a diagnostic test for determining a health state in a patient, in which a plurality of biomarkers (e.g., 10-300 biomarkers) are detected in a legacy clinical sample through the use of a corresponding plurality of immunoassays, where the total amount of the legacy clinical sample that is used across the plurality of immunoassays is less than about 1 mL (e.g., less than about 0.05 mL). Typically, multiple legacy clinical samples are analyzed in the same fashion, and the detected biomarkers are then analyzed for an association with the disease.

In another embodiment, a diagnostic test is used to screen or monitor a patient for a given health state. The test is developed using any of the methods disclosed herein for screening legacy clinical samples. For example, at least one biomarker indicative of the presence, absence, or likelihood of developing the health state and identified by the methods described herein is employed in the test and its presence, absence, or level is determined.

Other features and advantages of the invention will be apparent from the following detailed description and claims.

BRIEF DESCRIPTION OF THE DRAWINGS

For a better understanding of the present invention, and not intending to limit the scope of the invention in any way, reference is made to the following description, taken in conjunction with the accompanying drawings, in which like reference characters refer to like parts throughout, and in which:

FIG. 7 shows, without intending any limitation, the detection limit of selected biomarker assay technologies that are commercially available, indicating their typical analytical reproducibility performance characteristic (coefficient of variation) at these starting analyte concentrations. There are many additional technologies being applied to improve the sensitivity of single molecule detection, including microscopic techniques (atomic force microscopy, magnetic resonance force microscopy, scanning electrochemical microscopy, scanning tunneling microscopy) and spectroscopic techniques (fluorescence correlation spectroscopy, evanescent wave induced fluorescence spectroscopy, scanning near-field optical microscopy, scanning enhanced raman spectroscopy, surface plasma resonance).

DETAILED DESCRIPTION OF THE INVENTION

Figure 1:
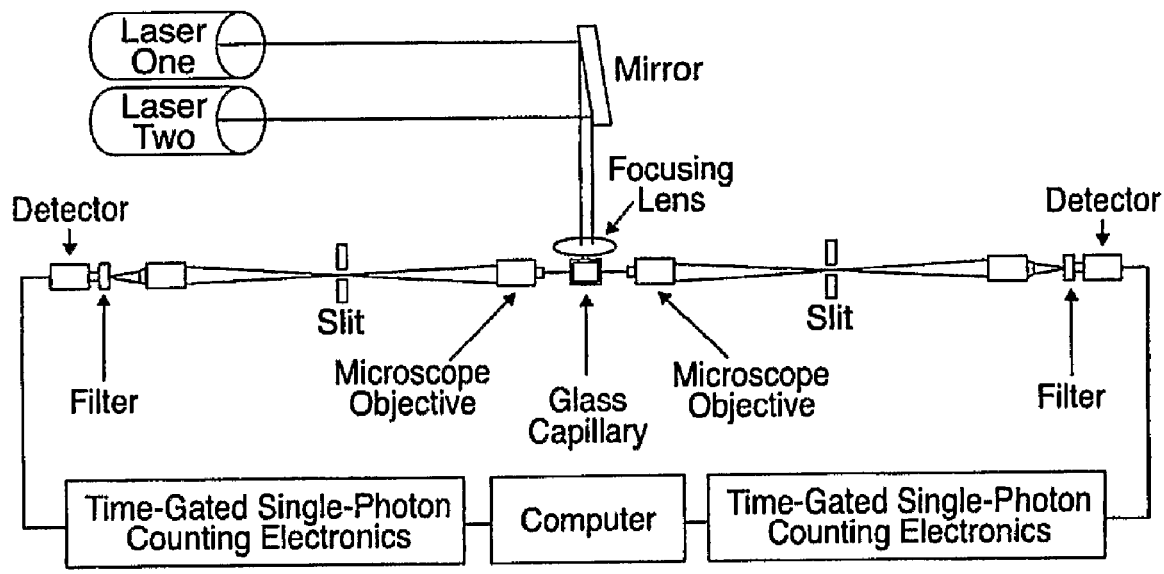
FIGS. 1 and 2 are illustrative diagrams of a single molecule detector in accordance with an embodiment of the present invention.

Embodiments of the present invention relate to systems and methods for developing diagnostic tests for diagnosing, and predicting the future development of, various health states (e.g., health states including disease-specific states as well as other non-disease specific states) in a subject. Examples of diseases are osteoporosis, pre-osteoporosis, diabetes, cancer, and any other disease. In one embodiment of the present invention, systems and methods are provided for developing diagnostic tests based on biomarker information from legacy clinical sample sets, for which only small sample sizes (e.g., about 0.05 to 1.0 mL or less) are typically available. In a preferred embodiment, the biomarker information is extracted from the clinical samples through the use of single molecule detection.

DEFINITIONS

"Biomarker" in the context of the present invention encompasses, without limitation, proteins, nucleic acids, and metabolites, together with their polymorphisms, isoforms, mutations, derivatives, variants, modifications, and precursors, including nucleic acids and pro-proteins, cleavage products, receptors (including soluble and transmembrane receptors), subunits, fragments, ligands, protein-ligand complexes, multimeric complexes, and degradation products, elements, related metabolites, and other analytes or sample-derived measures. Biomarkers can also include mutated proteins or mutated nucleic acids. Biomarkers also include any calculated indices created mathematically or combinations of any one or more of the foregoing measurements, including temporal trends and differences. The term "analyte" as used herein can mean any substance to be measured and can encompass electrolytes and elements, such as calcium.

"Clinical parameters" encompasses all non-sample or non-analyte markers of subject health status or other characteristics, such as, without limitation, age (AGE), ethnicity (RACE), gender (SEX), diastolic blood pressure (DBP) and systolic blood pressure (SBP), family history (FHX), height (HT), weight (WT), waist (Waist) and hip (Hip) circumference, body-mass index (BMI), past Gestational Diabetes Mellitus (GDM), resting heart rate, EMG, EEG, body temperature, and sleep states.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value". Non-limiting examples of "formulas" include sums, ratios, and regression operators, such as coefficients or exponents, biomarker value transformations and normalizations (including, without limitation, those normalization schemes based on clinical parameters, such as gender, age, or ethnicity), rules and guidelines, statistical classification models, and neural networks trained on historical populations. Of particular use in combining markers are linear and non-linear equations and statistical classification analyses to determine the relationship between levels of the biomarkers detected in a subject sample and the subject's risk of disease (for example). In panel and combination construction, of particular interest are structural and synactic statistical classification algorithms, and methods of risk index construction, utilizing pattern recognition features, including established techniques such as cross correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shruken Centroids (SC), StepAIC, Kth-Nearest Neighbor, Boosting, Decision Trees, Neural Networks, Bayesion Networks, Support Vector Machines, and Hidden Markov Models, among others. Many of these techniques are useful either combined with a biomarker selection technique, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Leave-One-Out (LOO) and 10-Fold cross-validation (10-Fold-CV).

"Frank Disease" in the context of the present invention, is a clearly manifest, unmistakable, evident, or symptomatic disease state that unequivocally meets the definition of the disease set forth by a professional medical organization, such as the World Health Organization.

"Health state" encompasses disease states (e.g., presence, absence, or risk of developing a disease and likely responses to therapies for the disease) as well as other states not necessarily related to a specific disease such as environmental exposure, nutritional status, neurological function, immune status, organ function, and blood chemistry. Generally, determining a health state in a patient/subject involves determining that the patient should be classified within a given one of a plurality of populations (e.g., healthy vs. unhealthy, in a 2-population example).

A "legacy subject" is a subject (defined below) for which one or more clinical samples is included in a legacy clinical sample set.

A "live subject" is a subject for whom a determination (e.g., diagnosis or prognosis of disease) is made by a diagnostic test that has been developed in accordance with the principles of the present invention.

A "legacy clinical sample" is a clinical sample for an individual from a legacy clinical sample set (which set may have multiple samples for multiple individuals), where the volume of the sample meets a sample requirement (defined below) and the biomarker information from the sample may be used to develop a diagnostic test in accordance with the principles of the present invention.

A "live clinical sample" is a clinical sample from which biomarker information is evaluated by a diagnostic test in order to provide a determination (e.g., diagnosis or prognosis) for a corresponding live subject.

"Measuring" or "measurement" means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters. Alternatively, the term "detecting" or "detection" may be used and is understood to cover all measuring or measurement as described herein.

"Risk" in the context of the present invention, relates to the probability that an event will occur over a specific time period (e.g., conversion to frank Diabetes) and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula $p/(1-p)$ where p is the probability of event and $(1-p)$ is the probability of no event) to no-conversion. Alternative continuous measures which may be assessed in the context of the present invention include time to health state (e.g., disease) conversion and therapeutic conversion risk reduction ratios.

"Pre-Disease" in the context of the present invention refers to a state that is intermediate between that defined as the normal homeostatic and metabolic state and states seen in Frank Disease. Pre-disease states can include abnormalities of homeostatic regulation, abnormal physiological measurements, abnormal morphometric measurements, and/or states in which abnormal levels of clinical parameters or biomarkers are present at a specific time point. Abnormalities are measurement outside the normal range as defined by professional medical organizations, such as the World Health Organization. "Pre-Disease" states, in the context of the present invention, are states, in an individual or in a population, having a higher than normal expected rate of disease conversion to frank disease. When a continuous measure of Pre-Disease conversion risk is produced, having a "pre-disease condition" encompasses any expected annual rate of conversion above that seen in a normal reference or general unselected normal prevalence population.

"Risk evaluation," or "evaluation of risk" in the context of the present invention encompasses making a prediction of the probability, odds, or likelihood that an event or health state may occur, the rate of occurrence of the event or conversion from one health state to another (e.g., from a normoglycemic condition to a pre-diabetic condition or pre-Diabetes, or from a pre-diabetic condition to pre-Diabetes or Diabetes). Risk evaluation can also comprise prediction of future levels, scores or other indices of disease, either in absolute or relative terms in reference to a previously measured population. The methods of the present invention may be used to make continuous or categorical measurements of the risk of conversion between health states. Embodiments of the invention can also be used to discriminate between normal and pre-diseased subject cohorts. In other embodiments, the present invention may be used so as to discriminate pre-diseased from diseased, or diseased from normal. Such differing use may require different biomarker combinations in individual panel, mathematical algorithm(s), and/or cut-off points, but be subject to the same aforementioned measurements of accuracy for the intended use.

A "sample" in the context of the present invention is a biological sample isolated from a subject and can include, by way of example and not limitation, whole blood, serum, plasma, blood cells, endothelial cells, tissue biopsies, lymphatic fluid, ascites fluid, interstitial fluid (also known as "extracellular fluid" and encompasses the fluid found in spaces between cells, including, inter alia, gingival crevicular fluid), bone marrow, cerebrospinal fluid (CSF), saliva, mucous, sputum, sweat, urine, or any other secretion, excretion, or other bodily fluids.

A "sample requirement" is the volume of starting sample required by a given assay technology in order to achieve an acceptable level of performance (coefficient of variation).

A "subject" in the context of the present invention is preferably a mammal. The mammal can be a human, non-human primate, mouse, rat, dog, cat, horse, or cow, but are not limited to these examples. Mammals other than humans can be advantageously used as subjects that represent animal models of disease, pre-disease, or a pre-disease condition. A subject can be male or female. A subject can be one who has been previously diagnosed or identified as having a health state (e.g., disease, pre-disease, or a pre-disease condition), and optionally has already undergone, or is undergoing, a therapeutic intervention for the health state. Alternatively, a subject can also be one who has not been previously diagnosed as having a given health state. For example, a subject can be one who exhibits one or more risk factors for a disease, pre-disease, or a pre-disease condition, or a subject who does not exhibit disease risk factors, or a subject who is asymptomatic for a disease, pre-disease, or pre-disease conditions. A subject can also be one who is suffering from or at risk of developing disease, pre-disease, or a pre-disease condition.

"Traditional laboratory risk factors" correspond to biomarkers isolated or derived from subject samples and which are currently evaluated in the clinical laboratory and used in traditional global risk assessment algorithms (e.g., Stern, Framingham, Finland Diabetes Risk Score, ARIC Diabetes, and Archimedes). Traditional laboratory risk factors commonly tested from subject blood samples include, but are not limited to, total cholesterol (CHOL), LDL (LDL/LDLC), HDL (HDL/HDLC), VLDL (VLDLC), triglycerides (TRIG), glucose (including, without limitation, the fasting plasma glucose (Glucose) and the oral glucose tolerance test (OGTT)) and HBA1c (HBA1C) levels.

INDICATIONS OF THE INVENTION

Embodiments of the present invention allow for the determining of a health state in a patient. For example, the risk of developing disease, pre-disease, or a pre-disease condition typically can be detected with a pre-determined level of predictability by measuring an "effective amount" of a biomarker in a test sample (e.g., a subject derived sample), and comparing the effective amounts to reference or index values, often utilizing mathematical algorithms or formulas in order to combine information from results of multiple individual biomarkers and from non-analyte clinical parameters into a single measurement or index. When appropriate, subjects identified as having an increased risk for a health state can optionally be selected to receive treatment regimens, such as administration of prophylactic or therapeutic compounds, or implementation of exercise regimens or dietary supplements to prevent or delay the onset of, for example, disease, pre-disease, or a pre-disease condition or other adverse heath conditions.

The amount of the biomarker can be measured in a test sample and compared to a normal control level, utilizing techniques such as reference limits, discrimination limits, or risk defining thresholds to define cutoff points and abnormal values for a health state. The normal control level means the level of one or more biomarkers or combined biomarker indices typically found in a subject not having the health state. Such normal control level and cutoff points may vary based on whether a biomarker is used alone or in a formula combining with other biomarkers into an index. Alternatively, the normal control level can be a database of biomarker patterns from previously tested subjects who did not convert to the health state over a clinically relevant time horizon.

The present invention may be used to make continuous or categorical measurements of the risk of conversion to an adverse health state (e.g., disease), thus diagnosing and defining the risk spectrum of a category of subjects defined as predisposed to the adverse health state. In the categorical scenario, the methods of the present invention can be used to discriminate between (for example) normal and pre-diseased subject cohorts. In other embodiments, the present invention may be used so as to discriminate pre-disease from disease, or diseased from normal. Other non-disease specific health states can also be determined. Such differing use may require different biomarker combinations in individual panel, mathematical algorithm, and/or cut-off points, but be subject to the same aforementioned measurements of accuracy for the intended use.

Identifying patients that are predisposed to adverse health states (e.g., pre-disease states) enables the selection and initiation of various therapeutic interventions or treatment regimens in order to delay, reduce or prevent those patients' conversion to the adverse health states (e.g., disease). Levels of a specific amount of biomarker also may allow for the course of treatment of the health state (e.g., disease, pre-disease, or a pre-disease condition) to be monitored. For example, in this method, a biological sample can be provided from a subject undergoing treatment regimens, e.g., drug treatments, for a disease. Such treatment regimens can include, but are not limited to, exercise regimens, dietary supplementation, weight loss, surgical intervention, device implantation, and treatment with therapeutics or prophylactics used in subjects diagnosed or identified with various health states. If desired, biological samples are obtained from the subject at various time points before, during, or after treatment.

The present invention can also be used to screen patient or subject populations in any number of settings. For example, a health maintenance organization, public health entity or school health program can screen a group of subjects to identify those requiring interventions, as described above, or for the collection of epidemiological data. Insurance companies (e.g., health, life or disability) may screen applicants in the process of determining coverage or pricing, or existing clients for possible intervention. Data collected in such population screens, particularly when tied to any clinical progression to conditions like disease, pre-disease, or a pre-disease condition, will be of value in the operations of, for example, health maintenance organizations, public health programs and insurance companies. Such data arrays or collections can be stored in machine-readable media and used in any number of health-related data management systems to provide improved healthcare services, cost effective healthcare, improved insurance operation, etc. See, for example, U.S. patent application No.; U.S. Patent Application No. 2002/0038227; U.S. Patent Application No. US 2004/0122296; U.S. Patent Application No. US 2004/0122297; and U.S. Pat. No. 5,018,067, which are hereby incorporated by reference herein in their entireties. Such systems can access the data directly from internal data storage or remotely from one or more data storage sites. Thus, in a health-related data management system, wherein risk of developing a diabetic condition for a subject or a population comprises analyzing disease risk factors, the present invention provides an improvement comprising use of a data array encompassing the biomarker measurements as defined herein and/or the resulting evaluation of risk from those biomarker measurements.

A machine-readable storage medium can comprise a data storage material encoded with machine readable data or data arrays which, when using a machine programmed with instructions for using said data, is capable of use for a variety of purposes, such as, without limitation, subject information relating to health state risk factors over time or in response to drug therapies, drug discovery, and the like. Measurements of effective amounts of the biomarkers of the invention and/or the resulting evaluation of risk from those biomarkers can be implemented in computer programs executing on programmable computers, comprising, inter alia, a processor, a data storage system (including volatile and non-volatile memory and/or storage elements), at least one input device, and at least one output device. Program code can be applied to input data to perform the functions described above and generate output information. The output information can be applied to one or more output devices, according to methods known in the art. The computer may be, for example, a personal computer, microcomputer, or workstation of conventional design.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein. The health-related data management system of the invention may also be considered to be implemented as a computer-readable storage medium, configured with a computer program, where the storage medium so configured causes a computer to operate in a specific and predefined manner to perform various functions described herein. Levels of a specific amount of one or more biomarkers can then be determined and compared to a reference value, e.g. a control subject or population whose state is known or an index value or baseline value. The reference sample or index value or baseline value may be taken or derived from one or more subjects who have been exposed to the treatment, or may be taken or derived from one or more subjects who are at low risk of developing a health state (e.g., disease, pre-disease, or a pre-disease condition), or may be taken or derived from subjects who have shown improvements in risk factors (such as clinical parameters or traditional laboratory risk factors as defined herein) as a result of exposure to treatment. Alternatively, the reference sample or index value or baseline value may be taken or derived from one or more subjects who have not been exposed to the treatment. For example, samples may be collected from subjects who have received initial treatment for disease, pre-disease, or a pre-disease condition and subsequent treatment for disease, pre-disease, or a pre-disease condition to monitor the progress of the treatment. A reference value can also comprise a value derived from risk prediction algorithms or computed indices from population studies such as those disclosed herein.

The biomarkers of the present invention can thus be used to generate a reference biomarker profile of those subjects who do not have a health state (e.g., impaired glucose tolerance in the case of Diabetes), and would not be expected to develop the health state. The biomarkers disclosed herein can also be used to generate a subject biomarker profile taken from subjects who have a health state such as disease, pre-disease, or a pre-disease condition. The subject biomarker profiles can be compared to a reference biomarker profile to diagnose or identify subjects at risk for developing the health state, to monitor the progression of the health state (e.g., disease), as well as the rate of progression of the health state, and to monitor the effectiveness of any treatments for the health state. The reference and subject biomarker profiles of the present invention can be contained in a machine-readable medium, such as but not limited to, digital and analog media like those readable by a VCR, CD-ROM, DVD-ROM, USB flash media, among others. Such machine-readable media can also contain additional test results, such as, without limitation, measurements of clinical parameters and traditional laboratory risk factors. Alternatively or additionally, the machine-readable media can also comprise subject information such as medical history and any relevant family history. The machine-readable media can also contain information relating to other disease-risk algorithms and computed indices such as those described herein.

A diagnostic test that is developed in accordance with the principles of the present invention can be used to make a determination for a live subject (e.g., a diagnosis or prognosis) based, at least in part, on the presence or level(s) of one or more biomarkers present in a live clinical sample from the live subject. The levels are determined, as is understood to those of ordinary skill in the art, within the sensitivity and specificity parameters of the test format selected (e.g., a biomarker is "absent" if its level is below the test's limit of detection or some other cut-off value). For example, one such diagnostic test may involve comparing the subject's biomarker level(s) to a reference value. As another example, the diagnostic test may involve evaluating the live subject's biomarker level(s) (and optionally other information for the subject such as, for example, age, weight, ethnicity, medical history, and/or other clinical information) with a formula or model that produces a diagnostic or prognostic score for the live subject.

A diagnostic test for a given health state may be developed, at least in part, through the use of a legacy clinical sample set. The legacy clinical sample set may include samples for a cohort of legacy subjects, for whom at least some data is known regarding the presence or absence of the health state. For example, a diagnostic test may be developed based on samples for legacy subjects who are known to have a given disease. Alternatively or additionally, the diagnostic test may be developed based on clinical samples for legacy subjects who are known to lack the disease or other health state.

Theoretically, an almost limitless number of biomarkers are available for selection within the process of developing a diagnostic test. However, only a subset of all available biomarkers (e.g., between 10 and 300) are typically selected per disease area, which subset of biomarkers may be identified by physicians and/or other sources of information (e.g., medical journals) with expertise in the disease area. Biomarkers may also be derived from de novo research using "open" proteomics profiling technologies such as mass spectrometry, LC-LC mass spectrometry, 2-D gel electrophoresis, protein arrays, western blots, reverse western tissue blots, etc.

In an embodiment of the present invention, systems and methods are provided for developing a diagnostic test, according to which (i) a set of one or more legacy clinical samples is received (e.g., 50 to 5000 legacy samples), (ii) the levels of a selected subset of biomarkers are measured from the sample(s), and (iii) the biomarker levels (and optionally clinical parameters) are analyzed for an association with the health state under consideration. This analyzing may involve, for example, using statistical analysis to determine whether a particular one or more biomarkers (and optionally particular level(s) of those biomarkers and/or clinical parameters) is correlated statistically with the presence, absence, or risk of developing the health state (e.g., progression to disease states of different severities), and/or to select one or more therapies or to monitor therapy response/efficacy. In some embodiments, a biomarker panel can be constructed and a formula derived specifically to enhance performance for use also in subjects undergoing therapeutic interventions, or a separate panel and formula may alternatively be used solely in such patient populations. An aspect of the invention is the use of specific known characteristics of biomarkers and their changes in such subjects for such panel construction and formula derivation. Such modifications may enhance the performance of various indications noted above in prevention of adverse health states, and diagnosis, therapy, monitoring, and prognosis of a health state. The biomarkers may vary under therapeutic intervention for the health state, whether lifestyle (e.g. diet and exercise), surgical (e.g., bariatric surgery) or pharmaceutical (e.g., one of the various classes of drugs mentioned herein or known to modify common risk factors or risk of disease) intervention. The biomarkers may also vary based on environmental exposure, nutritional status, neurological function, immune status, organ function, and/or blood chemistry. Alternatively or additionally, the analyzing of the biomarker may involve determining whether the inclusion of particular biomarker(s) in a formula or machine learning analysis (e.g., support vector or neural network analysis) increases the relative ability of a mathematical function resulting from the analysis to diagnose or predict the health state in a subject. Generally, machine learning is a form of artificial intelligence whereby information learned from a computer-assisted analysis of data can be used to generate a function that describes dependencies in data. This computer-assisted, machine learning analysis may be performed by any suitable software, hardware, or combination thereof (a "machine learning tool"). Suitable examples of machine learning tools will be apparent to those of ordinary skill in the art and therefore will not be described in detail.

A key feature of embodiments of the invention is the ability to profile tens, hundreds or even thousands of biomarkers in a single small legacy sample. It will be apparent that the invention thus allows the profiling of several classes of biomarkers, and the testing of multiple members of each class, in order to gain insight into the biological mechanisms of a health state and the interaction of such biomarkers. In the preferred embodiment, this encompasses two or more biomarker members per class, more preferably five or more, and most preferably ten or more. As will be appreciated by one skilled in the art, such classes include, without limitation, cytokines and chemokines, such as chemoattractants and inflammatory molecules such as acute phase reactants, signaling molecules, adhesion molecules, biomarkers of immunity (including subclasses, such as those related to individual immune cell lines such as macrophages, T-cells, neutrophils, eosinophils, etc), biomarkers of angiogenesis and endothelial function, and biomarkers of glucose and lipid metabolism and energy storage. Several of these classes overlap, in particular with respect to the cytokine, chemokine, and growth factor members of each. Selected representative examples of such classes and their members are given in the table below, without limiting the foregoing in any way.

Figure 6:
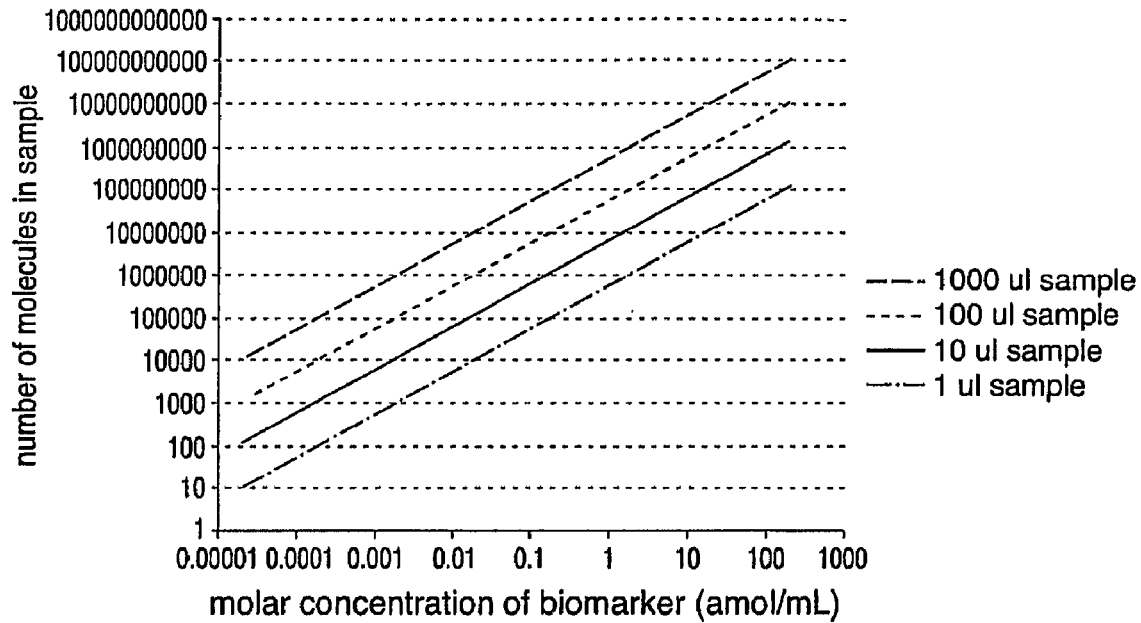
FIG. 6 shows a table indicating the actual number of analyte molecules present in a sample across the ranges of various sample sizes and starting analyte molar concentrations.
Figure 6:
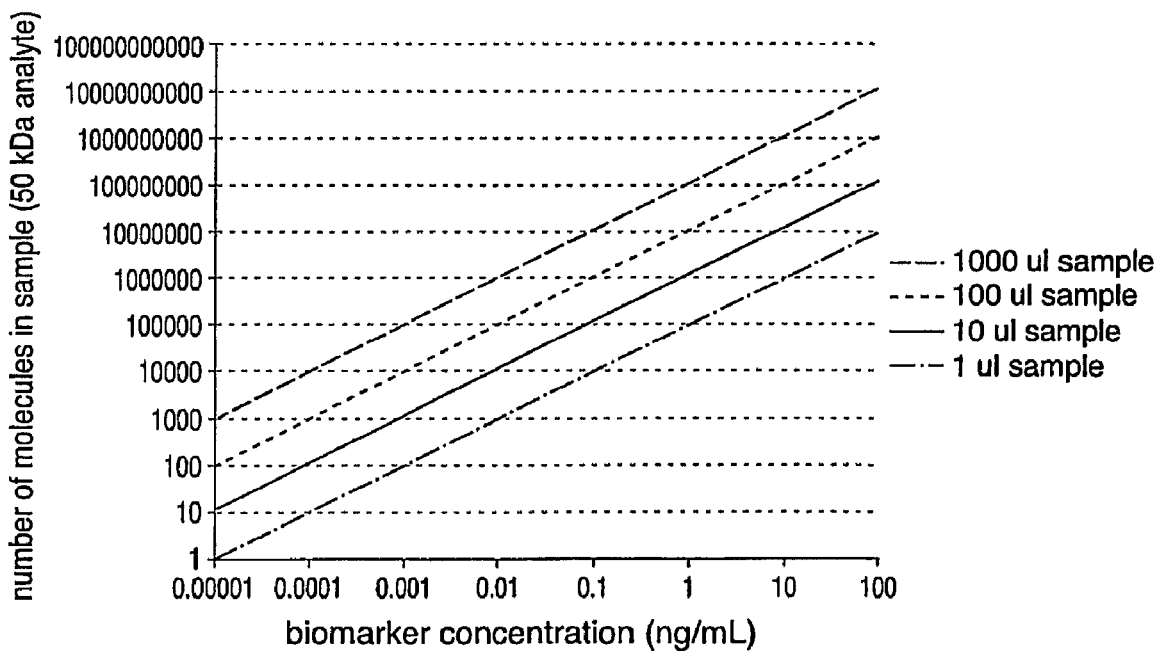

Biomarkers of Cardiovascular Disease", J Physiol 563.1 pp 23-60 (2005), and Anderson, "A List of Candidate Cancer Biomarkers for Targeted Proteomics", Biomarker Insights 2: 1-48 (2006), which are hereby incorporated by reference herein in their entireties. As shown in the table below and in FIG. 6, this range of concentrations rapidly approaches single molecule requirements, particularly when combined with the smaller volume samples commonly available in legacy clinical sample sets.

| Concentration of 50 kDa molecule | pg/mL | amol/mL | Molecules/mL |
|---|---|---|---|
| 50 mg/mL | 50,000,000,000 | 1,000,000,000 | $6.02 \times 10^{17}$ |
| 10 mg/mL | 10,000,000,000 | 200,000,000 | $1.02 \times 10^{17}$ |
| 1 mg/mL | 1,000,000,000 | 20,000,000 | $1.02 \times 10^{16}$ |
| 100 ug/mL | 100,000,000 | 2,000,000 | $1.02 \times 10^{15}$ |
| 10 ug/mL | 10,000,000 | 200,000 | $1.02 \times 10^{14}$ |
| 1 ug/mL | 1,000,000 | 20,000 | $1.02 \times 10^{13}$ |
| 100 ng/mL | 100,000 | 2,000 | $1.02 \times 10^{12}$ |
| 10 ng/mL | 10,000 | 200 | $1.02 \times 10^{11}$ |
| 1 ng/mL | 1,000 | 20 | $1.02 \times 10^{10}$ |
| 100 pg/mL | 100 | 2 | $1.02 \times 10^{9}$ |
| 10 pg/mL | 10 | 0.2 | $1.02 \times 10^{8}$ |
| 1 pg/mL | 1 | 0.02 | $1.02 \times 10^{7}$ |

Concentration ranges of common biomarkers within the plasma proteome, indicating the disagreement of biomarker

| Examples of Classes of Molecules | Examples of Genes and Molecules in the Class |
|---|---|
| Acute Phase Reactants | SAA1, CRP, IL1, IL6, IL8, TNFA, FTL, A2M. MBL, SAP |
| Angiogenesis & Endothelial Function | VEGF, CD36, ANG1, ANG2/ANGPT2, ENG, FGF2, PDGF |
| Cell Adhesion | ICAM, DPP4/CD26, CD38, SELE, SELP, CD62L, VCAM, ITGA1, ITGA2, ITGA4, ITGAL, ITGAX, ITGB1, ITGB2, ITGB3 |
| Cell Proliferation & Death | AKT1, CASP2, CASP8, CASP9, IGF, TNF/TNFA, TNFR1, TNFSF10, TNFSF11, CDK2, FAS, FASLG |
| Chemokines | CCL1, MCP-1/CCL2, CCL3, CCL4, CCL5, CCL6, MCP-3/CCL7, MCP-2/CCL8, CCL9, CCL11, CCL12, MCP-4/CCL13, CCL19, CCL21, CCL24, CCL26, CCL27, CXCL1, CXCL2, IP10/CXCL10, IL8, CX3CL1 |
| Cytokines | IL1B, IL1RN, IL2, IL3, IL4, IL5, IL6, IL8, IL10, IL12, IL12B, IL13, IL18, BTC, TGFA, TGFB, TNF, CSF1, CSF2, CSF3, IFNG |
| Coagulation | C2, C3, C4, C5, C9, C1, F2, F12, PROC, PROS1, SERPING1, FGA, VWF, D-dimer |
| Growth Factors & Hormones | EGF, GH1, NGFB, ADIPOQ, IGF, CSF1, CSF2, CSF3, PDGF, EPO, FGF2, GDF8, GDF9, GH1, IGF1, TGFB1, TPO, EFG, HGF, FGF, IGF, BMP1, BMP2, BMP3, BMP7 |
| Inflammation | CSF1, CSF2, CSF3, IFNG, CD40LG, CD40, C3, C5A, TNF, IL1, IL8, SELP, |
| Lipid Metabolism | Lipoprotein(a), LEP, ADIPOQ, AGRP, NPY |
| Energy Homeostasis | INS, glucose, HBA1c, C-peptide, IGF-1, AKT2 |
| Proteolysis | MMP2, MMP9, SERPINA1, heparin, SERPIND1, PAI-1/SERPINE1, TIMP1, TIMP2, CASP3 |

Figure 5:
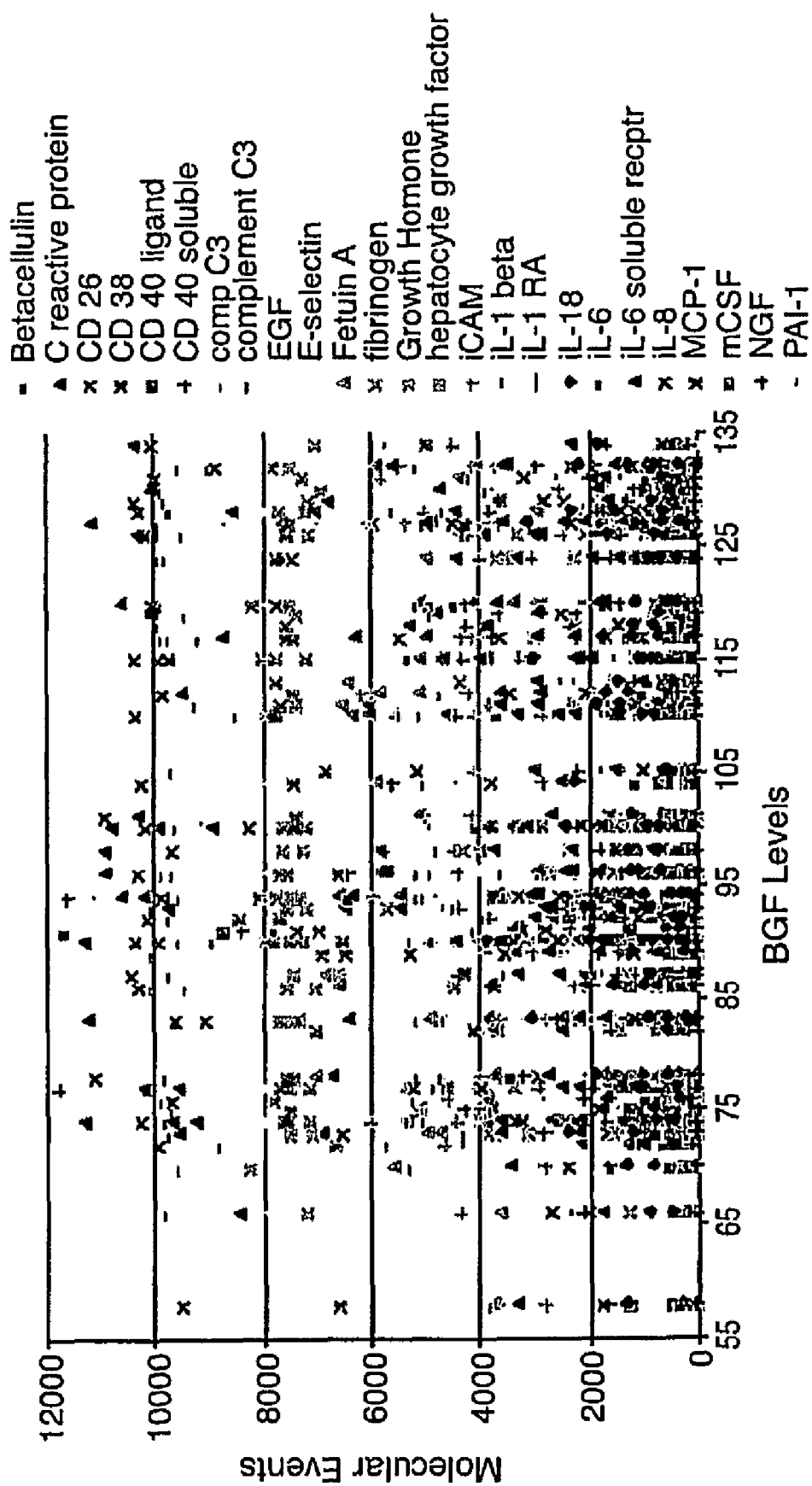
FIG. 5 shows illustrative single molecule detection data in accordance with an embodiment of the present invention.

Another key aspect of the invention is, in a preferred embodiment, utilizing a single molecule detector, with the ability to range multiple orders of concentration magnitude by using the stochastic and quantum nature of single molecule detection. In particular, biomarkers within the plasma proteome, including many of those cited above, are known to span many orders of magnitude in their molar concentration, as seen in the literature. Without limitation of the foregoing, a review of such concentrations cited from literature for cardiovascular and cancer related plasma proteins is described in Anderson, "Candidate-Based Proteomics in the Search for discovery technology such as mass spec across sample sets in the literature are also shown in Anderson et al., "The Human Plasma Proteome: History, Character, and Diagnostic Prospects", Molecular & Cellular Proteomics 1.11, pp. 845-867 (2002) and Anderson et at, "The Human Plasma Proteome: A Nonredundant List Developed By Combination of Four Separate Sources", Molecular & Cellular Proteomics 3.4, pp. 311-326 (2004), which are hereby incorporated by reference herein in their entireties. Such disagreement further demonstrates the different detection system needs inherent when encountering broad concentration ranges, which may occur both across many analytes and across many differing health states. FIG. 5 demonstrates the practice of the invention across multiple orders of magnitude in concentration, and across representative biomarkers of each of the aforementioned classes.

PRACTICE OF THE INVENTION

In a preferred embodiment, the biomarker levels are measured from the clinical sample(s) through the use of a single molecule detector. Suitable single molecule detection equipment is described in U.S. Patent Application Publication Nos. 2004/0166514 A1, 2005/0164205 A1, and 2006/0003333 A1, the disclosures of which are hereby incorporated by reference herein in their entireties. Other examples of single molecule detectors that can be used in accordance with preferred embodiments of the present invention are described in U.S. Patent Application Publication No. 2005/0221408, PCT Publication No. WO 2005/089524, and Richard Brown et al., "Review of Techniques for Single Molecule Detection in Biological Applications, National Physical Laboratory Report, 2001, the disclosures of which are hereby incorporated by reference herein in their entireties. Generally, a single molecule detector operates under the principle that the ultimate, and desired, detection of biomarker information occurs at the level of individual molecules, interactions between molecules, and molecular complexes. Such individual molecules, molecular interactions, and/or molecular complexes can be detected by flow cytometry, single molecule electrophoresis, ion-channel switch membrane biosensor, or other single-molecule analytical instrumentation. Single molecule information can be cumulated over multiple molecular events, providing dynamic quantification of biomarker levels within a clinical sample, allowing the sparing use of very small samples. Data acquisition of such events may be halted when a sufficient number of events are received within a given sample volume to reliably quantitate (e.g. reliably here meaning with a coefficient of variation of 20% or less) a given biomarker's concentration using a presumed Poisson or binomial probability distribution function, as known by one skilled in the art. Such dynamic quantitation of very small sample volumes is a key aspect of the invention as practiced using single molecule detectors.

Accordingly, embodiments of the present invention contemplate the specific application of single molecule detection to the development of diagnostic tests based on legacy clinical sample sets. Namely, it has been determined by the present inventors that single molecule detection can detect the presence of biomarker or levels thereof with a suitable sensitivity using only about 1 uL or less of sample per single-biomarker immunoassay (for example). Any suitable analyte recognition unit (e.g., antibodies, aptamers, molecular imprints, probes, primers etc. which have differentially greater affinity for a biomarker of interest) and signal detection technique can be used with a single molecule detection reader in accordance with the present invention. Additionally, it will be understood that the present invention is not limited to the use of immunoassays. Thus, for example, to develop a diagnostic test based on an initial subset of (for example) 300 biomarkers, the use of single molecule detection allows requires a sample size of only about 0.3 mL (i.e., 1 uL per assay*300 biomarkers), or about 0.9 mL if the assays are done in triplicate. The assay may use a 96-well, 384-well format or any other suitable assay configuration. Any multiplexing within the assay will only further reduce the required sample size. The present inventors have applied this knowledge to the discovery that diagnostic tests can be developed based on legacy clinical samples which, as described, are typically available in sizes of 0.05 to 1.0 mL or less. Additional details regarding an illustrative single molecule detection system are provided below.

Figure 2:
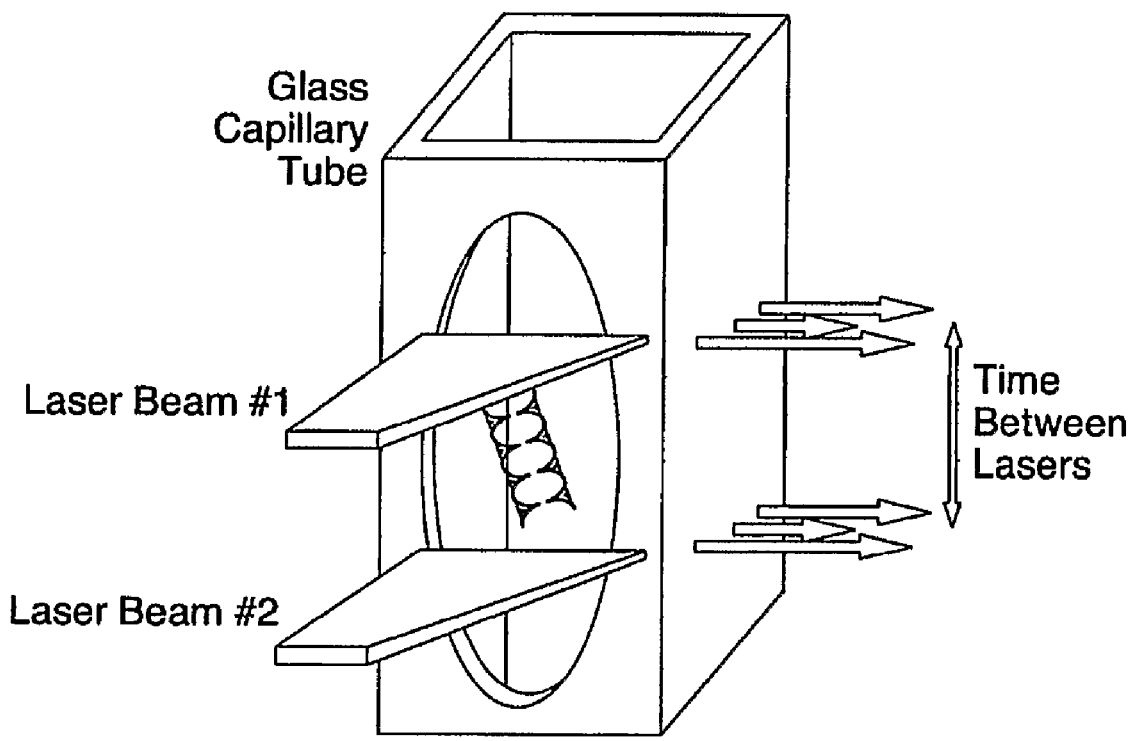

In some embodiments, the single molecule detection system can rely on single-molecule fluorescence. Thus, in such embodiments, no polymerases, enzymes or proteins, or any amplification processes are necessary so sample preparation times and complexity are minimal. In other embodiments, the single molecule detection may utilize labeled antibodies. Such labels for individual antibody (or other suitable biomarker recognition units) may themselves be constructed of a plurality of individual fluorescent molecules, further amplifying the signal derived from each single complex multi-fold, and further reducing the detection technique requirements for single molecule detection (such multiplexing of fluorophores may be achieved using beads, dedrimers, polysaccharides and other natural and synthetic polymers, amongst other techniques well described in the art). In one embodiment, the basic detection apparatus may comprise one or two lasers (or a single laser source split into two beams), focusing light-collection optics, one or two single photon detectors, and detection electronics under computer control. FIGS. 1 and 2 are illustrative diagrams of a single molecule detector in accordance with an illustrative, but non-limiting, embodiment of the present invention. A sample compartment is also included and may comprise two reservoirs that hold the solution being analyzed. The reservoirs can be connected by tubing to a glass capillary cell.

The system also may include a glass capillary flow cell. For example, two laser beams (5 um in diameter) are optically focused about 100 um apart and perpendicular to the length of the sample-filled capillary tube. The lasers generally are operated at particular wavelengths depending upon the nature of the detection probe to be excited. An interrogation volume of the detection system may be determined by the diameter of the laser beam and by the segment of the laser beam selected by the optics that direct light to the detectors. The interrogation volume is preferably set such that, with an appropriate sample concentration, single molecules (such as single biomarker-recognition unit hybrids, single nucleic acid probes or single probe-target hybrids) are present in the interrogation volume during each time interval over which observations are made. Another embodiment of an apparatus for use in accordance with the present invention uses the same capillary flow cell and detection system, but only uses a single laser beam and detector.

With the above-described instrument configuration (5 um laser beam) approximately 0.25% of the fluorescent molecules in the solution pass through the laser beams and are typically detectable. This percentage can be increased by configuring each laser beam such that it forms a narrow band perpendicular to the length of the capillary. Such an arrangement can raise the percentage of detectable molecules to approximately 5% of the molecules in the solution. Other configurations illuminating larger areas of the capillary have been calculated to enable detection of up to (for example) 50% of the fluorescent molecules present in a sample. The device has the capability of detecting single molecules in real time, allowing the detection of a fixed number of counts independent of time, and enabling dynamic quantification and concentration range finding during the course of the initial detection period. This feature allows faster readouts of samples as setting a count threshold (for example, at 1000 molecular events or such other effective level, giving a statistically valid quantitation of a biomarker within a sample) is often much faster than a fixed time point (1 minute). For higher biomarker concentrations, preparatory sample dilution may nonetheless be required in order to avoid reaching the count threshold too rapidly in such single molecule detector configurations.

Figure 3:
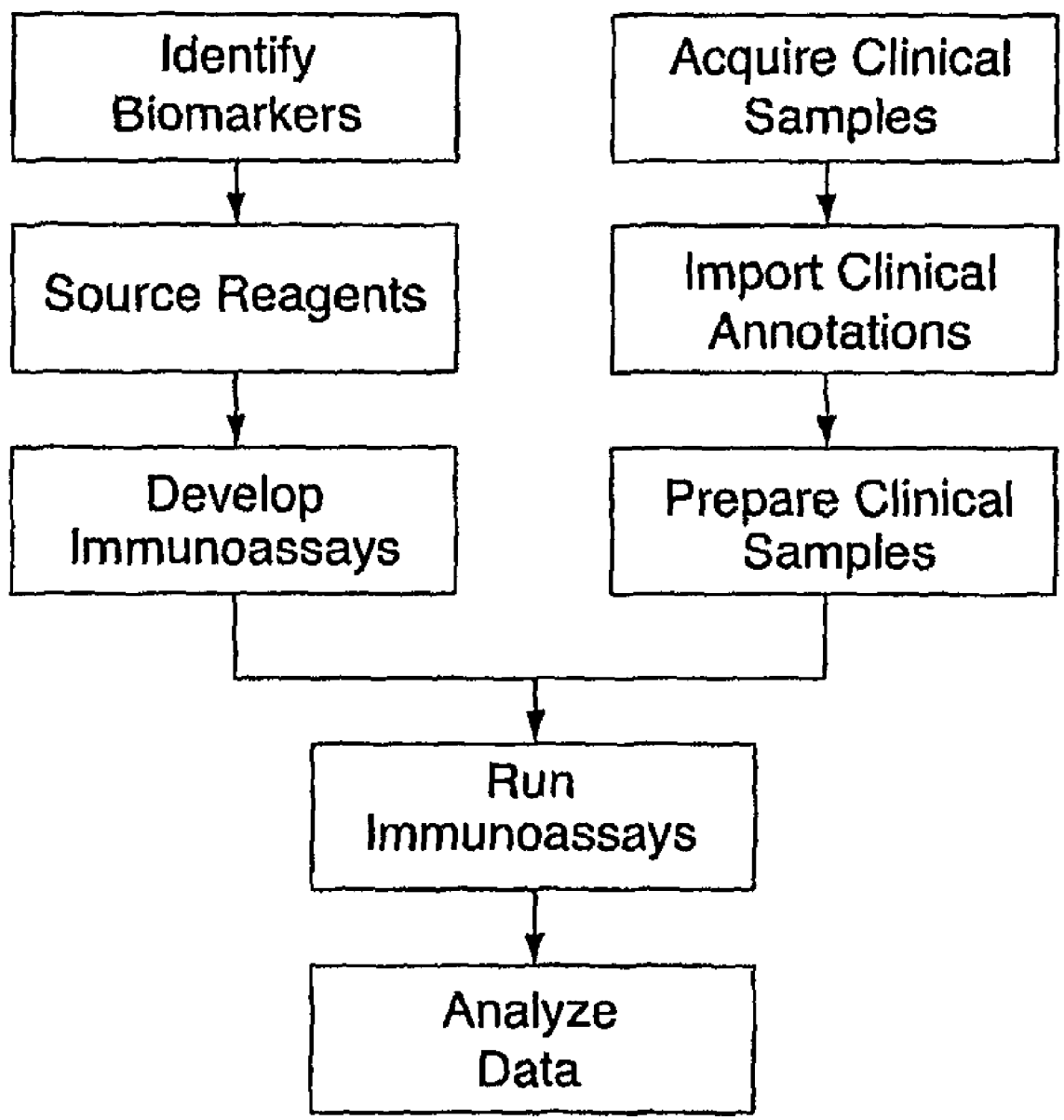
FIG. 3 is a flowchart of illustrative stages involved in developing a diagnostic test in accordance with an embodiment of the present invention.
Figure 4:
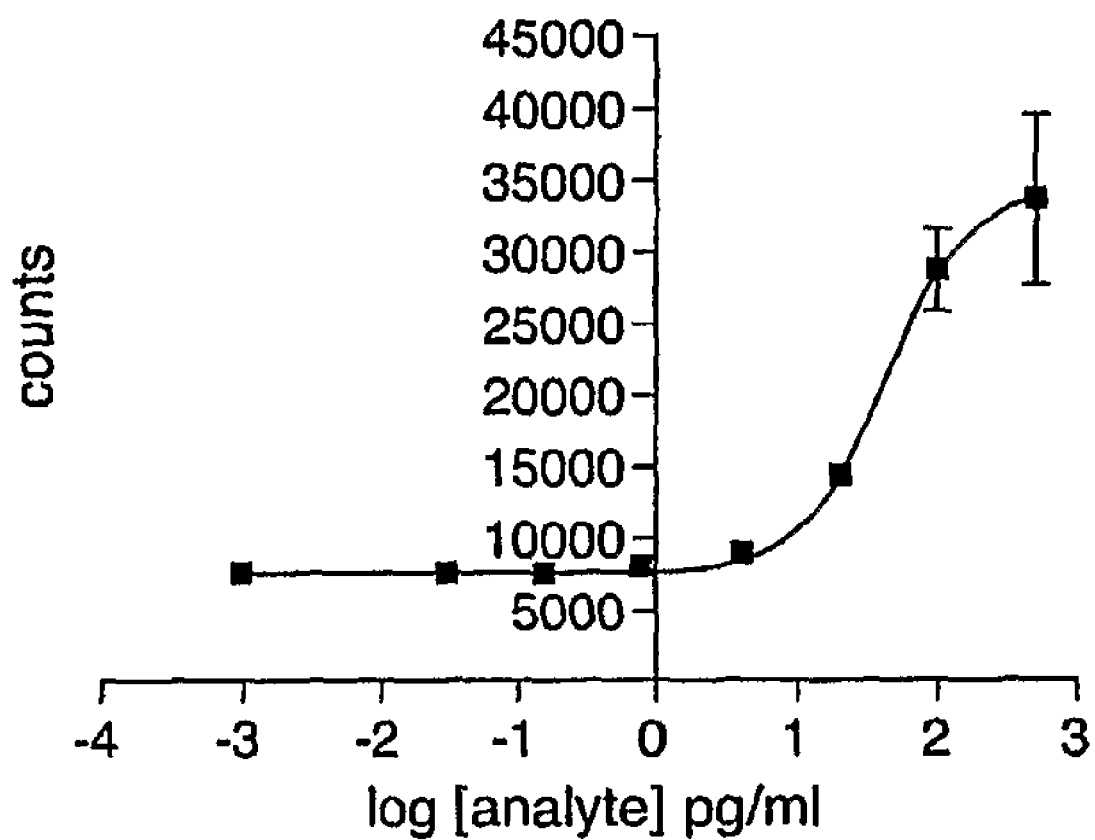
FIG. 4 shows a typical result for a working standard curve used in the development of immunoassays in accordance with an embodiment of the present invention.

FIG. 3 is a flowchart of illustrative, exemplary stages involved in developing a diagnostic test in accordance with some of the embodiments of the present invention, including: identification of biomarker candidates, sourcing of reagents, assay development, procurement of clinical samples, interrogation of clinical samples with biomarker assays, and analysis of the data to identify predictive markers and incorporate the results into predictive tests. These illustrative stages are described in greater detail below.

Identify biomarkers: Biomarkers may be identified by way of a comprehensive search through scientific and patent literature, supplemented with expert review. Based on an understanding of biological mechanisms associated with progression in a given disease area, standard search terms are developed to generate disease-specific databases containing typically thousands of journal articles and hundreds of patents. Cannonical pathways, homology, and linkage studies are alternative means of identifying putative biomarkers for a given disease state, as are cell line and animal experiments utilizing mRNA expression under response to stimuli, active agents (drugs, siRNAs, etc.), or in disease-specific organisms (knock-outs, nude mice, ApoE deficient mice, etc.) as are well known to those versed in the art of biomarker discovery. Analytical techniques on larger sample volumes, or pooled sample volumes, may also be used as in Granger, et al. Discovery of Proteins Related to Coronary Artery Disease Using Industrial-Scale Proteomics Analysis of Pooled Plasma, American Heart Journal v152 (3) September 2006, which is hereby incorporated by reference herein in its entirety. Each article and patent is read to identify candidates which are organized in a spreadsheet. For each biomarker, standardized nomenclature derived from human genome databases (e.g., www.ncbi.nlm.nih.gov/Entrez/) is applied to eliminate redundancy and enter standardized annotations.

A score for evidence level is assigned to prioritize the potential value of each biomarker based on experimental data. The evidence level may be combined with protein cellular expression localization to create an overall prioritized list of biomarkers for each disease. At the end of this process, the list of candidates is typically 150-400 biomarkers, but may be more or less. Illustrative lists of biomarkers for use in developing diagnostic tests for diabetes and osteoporosis are described in U.S. Provisional Patent Application Nos. 60/725,462, filed Oct. 11, 2005, 60/771,077, filed Feb. 6, 2006, Ser. No. 11/546,874, filed Oct. 11, 2006, Ser. No. 11/703,400, filed Feb. 6, 2007, and U.S. application Ser. No. 11/788,260, filed Apr. 18, 2007, titled "Diabetes-Associated Markers and Methods of Use Thereof", which are all hereby incorporated by reference herein in their entireties.

Source Reagents: Table 1 below shows a large and diverse array of vendors that may be used to source immunoreagents as a starting point for assay development. Using the prioritized list of markers, a search for capture antibodies, detection antibodies, and analytes may be performed that can be used to configure a working sandwich immunoassay.

For example, in one disease area, diabetes, 156 of 208 biomarkers were successfully sourced. Depending on the specific disease area, it is anticipated that anywhere from 50 to 80% of the biomarkers on any list are available from commercial sources. The reagents are ordered and received into inventory.

TABLE 1

| Immunoreagent Vendors | |
|---|---|
| Company | Website |
| Abazyme | http://www.abazyme.com/ |
| AbCam | http://www.abcam.com/ |
| AbGent | http://www.abgent.com/ |
| AbKem | http://www.abkemiberia.com/ |
| Abnova | http://www.abnova.com.tw/ |
| Absea Biotechnology | http://www.absea-antibody.com/ |
| Academy Biomed | http://www.academybiomed.com/ |
| Accurate Chemical and Scientific Corporation | http://www.accuratechemical.com/ |
| Acris | http://www.acris-antibodies.de/ |
| Advanced Immunochemical, Inc. | http://www.advimmuno.com/ |
| Advanced Targeting Systems | http://www.atsbio.com/ |
| Affibody | http://www.affibody.com/ |
| Affiniti Research Products Limited | http://www.affiniti-res.com/ |
| Affinity Biologicals | http://www.affinitybiologicals.com/ |
| Affinity Bioreagents | http://www.bioreagents.com/ |
| Alexis Biochemicals | http://www.alexis-corp.com/ |
| Alomone Labs | http://www.alomone.com/ |
| Alpha Diagnostic Intl. | http://www.4adi.com/ |
| AlphaGenix | http://www.alphagenix.com/ |
| American Diagnostica Inc. | http://www.amerciandiagnostica.com |
| American Qualex | http://www.americanqualex.com/ |
| American Research Products | http://www.arp1.com/ |
| American Type Culture Collection | http://www.atcc.org/ |
| Anaspec | http://www.anaspec.com/ |
| ANAWA Trading SA | http://www.anawa.ch/ |
| Ancell | http://www.ancell.com/ |
| AngioBio | http://www.angiobio.com/ |
| Angio-Proteomie | http://www.angioproteomie.com/ |
| Aniara | http://www.aniara.com/ |
| Anogen | http://www.anogen.ca/ |
| Antibodies Incorporated | http://antibodiesinc.com/ |
| AntibodyBcn | http://www.antibodybcn.com/ |
| AntibodyShop | http://www.antibodyshop.com/ |
| Apotech | http://www.apotech.com/ |

TABLE 1-continued

Immunoreagent Vendors

| Company | Website |
|---|---|
| APTEC Diagnostics | http://www.aptec.be/ |
| Araclon Biotech | http://www.araclonbiotech.com/ |
| Assay Designs | http://www.assaydesigns.com/ |
| Athens Research and Technology | http://www.athensresearch.com/ |
| Austral Biologicals | http://www.australbiologicals.com/ |
| Aves Labs | http://www.aveslab.com/ |
| Aviva Antibody | http://www.aviva-antibody.com/ |
| Axxora | http://www.axxora.com/ |
| Babraham Technix | http://www.babraham.com/ |
| Bachem | http://www.bachem.com/ |
| Beckman Coulter, Inc. | http://www.beckmancoulter.com/ |
| Bender Medsystems | http://www.bendermedsystems.com/ |
| Bethyl Laboratories | http://www.bethyl.com/ |
| Bio Research Canada | http://www.bioresearchcanada.com/ |
| BioCore | http://www.biocore.com.au/ |
| BioCytex | http://www.biocytex.fr/International.htm |
| Biodesign International | http://www.biodesign.com/ |
| Biogenesis | http://www.biogenesis.co.uk/ |
| BioGenex | http://www.biogenex.com/ |
| BioLegend | http://www.biolegend.com/ |
| Biomarket | http://www.biomarket.fi/ |
| Biomeda Corporation | http://www.biomeda.com/ |
| Biomedical Technologies | http://www.btiinc.com/ |
| BIOMOL International | http://www.biomol.com/ |
| BioProcessing | http://www.bioprocessinginc.com/ |
| Biosense Laboratories | http://www.biosense.com/ |
| BioSepra | http://www.biosepra.com/ |
| Biosonda | http://www.biosonda.com/ |
| BioSource International | http://www.biosource.com/ |
| BiosPacific | http://biospacific.com/ |
| Biostride | http://www.biostride.com/ |
| Biotrend | http://www.biotrend.com/index.html |
| Biovendor Laboratory Medicine | http://www.biovendor.com/ |
| Biovet | http://www.bvuco.com/ |
| BMA Biomedical | http://www.bma.ch/ |
| Boston Biochem | http://www.bostonbiochem.com/ |
| Brendan Scientific | http://www.brendan.com/ |
| Calbiochem | http://www.calbiochem.com/ |
| Caltag | http://www.caltag.com/ |
| Cambio | http://www.cambio.co.uk/ |
| CanAg Diagnostics | http://www.canag.se/ |
| Capralogics | http://www.capralogics.com/ |
| Capricorn Products | http://www.capricornproducts.com/ |
| Cayman Chemical Company | http://www.caymanchem.com/ |
| Cedarlane Laboratories | http://www.cedarlanelabs.com/ |
| Cell Marque | http://www.cellmarque.com/ |
| Cell Sciences | http://www.cellsciences.com/ |
| Cell Signaling Technology | http://www.cellsignal.com/ |
| Cemines | http://www.cemines.com/ |
| Chang Bioscience | http://www.changbioscience.com/ |
| Chemicon International | http://www.chemicon.com/ |
| Chemokine | http://www.chemokine.com/ |
| Clonegene | http://www.clonegene.com/ |
| Clontech | http://www.bdbiosciences.com/clontech/ |
| Cortex Biochem | http://www.cortex-biochem.com/ |
| Covance Research Products | http://www.crpinc.com/ |
| Cytolab | http://www.cytolab.com/ |
| Cytopulse | http://www.cytopulse.com/ |
| Cytoshop | http://www.cytoshop.com/ |
| CytoStore | http://www.cytostore.com/ |
| DAKO | http://www.dakocytomation.com/ |
| Deltabiolabs | http://www.deltabiolabs.com/ |
| Development Studies Hybridoma Bank | http://www.uiowa.edu/~dshbwww/ |
| Diaclone | http://www.diaclone.com/ |
| Diagnostic BioSystems | http://www.dbiosys.com/ |
| Diagnostic Systems Laboratory | http://www.dslabs.com/ |
| Diasorin | http://www.diasorin.com/ |
| Diatec | http://www.diatec.com/ |
| Dolfin | http://www.dolfinin.com/ |
| Dutch Diagnostics | http://www.dutch-diagnostics.com/ |
| East Coast Biologies | http://www.eastcoastbio.com/ |
| eBioscience | http://www.ebioscience.com/ |
| Echelon Research Laboratorie | http://www.echelon-inc.com/ |
| ECM Biosciences | http://www.ecmbiosciences.com/ |
| EnCor Biotechnology | http://www.encorbio.com/ |
| Endocrine Technologies | http://www.endocrinetech.com/ |

TABLE 1-continued

Immunoreagent Vendors

| Company | Website |
|---|---|
| Enzo Biochem | http://www.enzobio.com/ |
| Epitomics | http://www.epitomics.com/ |
| Euroclone | http://www.euroclone.net/ |
| Euro-Diagnostica | http://www.eurodiagnostica.com/ |
| Eurogentec | http://www.eurogentec.com/ |
| Everest Biotech | http://www.everestbiotech.com/ |
| Exalpha | http://www.exalpha.com/ |
| EXBIO Praha | http://www.exbio.cz/ |
| EY Laboratories | http://www.eylabs.com/ |
| FabGennix Int. | http://www.fabgennix.com/ |
| Fitzgerald Industries International | http://www.fitzgerald-fii.com/ |
| Fortron Bio Science | http://www.fortron.com/ |
| Fusion Antibodies | http://www.fusionantibodies.com/ |
| FutureImmune Immunologic Technical and Consulting Services | http://www.futureimmune.com/ |
| Gallus Immunotech | http://www.gallusimmunotech.com/ |
| G-Biosciences | http://www.gbiosciences.com/ |
| GEMAC | http://www.gemacbio.com/ |
| Genesis Biotech | http://www.genesisbio.com.tw/ |
| G-Biosciences | http://www.gbiosciences.com/ |
| Genex | http://www.genexbioscience.com/ |
| Genhot Laboratories | http://www.genhot.com.tw/ |
| Genway Biotech | http://www.genwaybio.com/ |
| GloboZymes | http://www.globozymes.com/ |
| Good Biotech | http://www.good-biotech.com/ |
| Green Mountain Antibodies | http://www.greenmoab.com/ |
| Groovy Blue Genes Biotech | http://www.groovybluegenes.com/ |
| Haematologic Technologies | http://www.haemtech.com/ |
| Hampton Research | http://www.hamptonresearch.com/ |
| Histoline Laboratoires | http://www.histo-line.it/ |
| HyCult Biotechnology | http://www.hbt.nl/ |
| HyTest | http://www.hytest.fi/ |
| IBL | http://www.ibl-hamburg.com/ |
| IBT | http://www.afsbio.de/ |
| IDS | http://www.idsltd.com/ |
| Imgenex | http://www.imgenex.com/ |
| IMMCO Diagnostics | http://www.immcodiagnostics.com/ |
| Immunodetect | http://www.immunodetect.com/ |
| Immunodiagnostik | http://www.immundiagnostik.com/ |
| ImmunoGlobe Antikoerpertechnik | http://immunoglobe.com/ |
| ImmunoKontact | http://www.immunokontact.com/ |
| ImmunologicalsDirect | http://www.immunologicalsdirect.com/ |
| Immunology Consultants Laboratory | http://www.icllab.com/ |
| Immunometrics | http://www.immunometrics.co.uk/ |
| Immuno-Precise Services | http://www.immuno-precise.com/ |
| Immunostar | http://www.immunostar.com/ |
| Immunostep | http://www.immunostep.com/ |
| ImmunoTools | http://www.immunotools.com/ |
| Immunovision | http://www.immunovision.com/ |
| Immuquest | http://www.immuquest.com/ |
| Biogenex | http://www.biogenex.com/ |
| Innova Biosciences | http://www.innovabiosciences.com/ |
| Innovation Automation | http://www.ia-one.com/ |
| Innovex | http://www.innvx.com/ |
| Insight Biotechnology | http://www.insightbio.com/ |
| International Enzymes | http://www.internationalenzymes.com/ |
| Invitek | http://www.invitek.de/ |
| Invitrogen | http://www.invitrogen.com/ |
| IQ Products | http://www.iqproducts.nl/ |
| Isconova | http://www.isconova.se/ |
| ISL (Immune Systems Ltd) | http://www.is-l.com/ |
| Jackson ImmunoResearch Laboratory | http://www.jacksonimmuno.com/ |
| KCH Scientific | http://www.kchscientific.com/ |
| Kirkegaard & Perry Laboratorie | http://www.kpl.com/ |
| KMI Diagnostics | http://www.kmidiagnostics.com/ |
| Koma Biotech | http://www.komabiotech.com/ |
| Kordia Laboratory Supplies | http://www.kordia.nl/ |
| Lab Vision Corporation | http://www.labvision.com/ |
| LabFrontier Life Science Institute | http://bio.labfrontier.com/ |
| LAE Biotechnology Company | http://www.laebio.com/ |
| Lampire Biological Laborator | http://www.lampire.com/ |
| Lee Laboratories | http://www.leelabs.com/ |
| Leinco Technologies | http://www.leinco.com/ |
| Lifescreen | http://www.lifescreen.com/ |
| Linco Research | http://www.lincoresearch.com/ |
| Maine Biotechnology Services | http://www.mainebiotechnology.com/ |

TABLE 1-continued

Immunoreagent Vendors

| Company | Website |
|---|---|
| MBL International | http://www.mblintl.com/ |
| Mediclone | http://business.vsnl.com/mediclone/ |
| Medix Biochemica | http://www.medixbiochemica.com/ |
| MedSystems Diagnostics GmbH | http://www.bendermedsystems.com/ |
| MicroPharm Ltd. | http://www.micropharm.co.uk/ |
| MilleGen | http://www.millegen.com/ |
| MitoSciences | http://www.mitosciences.com/ |
| MoBiTec | http://www.mobitec.de/ |
| ModiQuest | http://www.modiquest.com/ |
| Molecular Innovations | http://www.mol-innov.com/ |
| Molecular Probes | http://www.probes.com/ |
| MP Biomedicals | http://www.mpbio.com/ |
| Mubio Products | http://www.mubio.com/ |
| NatuTec | http://www.natutec.de/ |
| Neoclone | http://www.neoclone.com/ |
| Neuromics | http://www.neuromics.com/ |
| New England Biolabs | http://www.neb.com/ |
| Nordic Immunological Laboratories | http://www.nordiclabs.nl/ |
| Norrin Laboratories | http://www.norrinlabs.com/ |
| Novocastra | http://www.novocastra.co.uk/ |
| Novus Biologicals | http://www.novus-biologicals.com/ |
| OEM Concepts, Inc. | http://www.oemconcepts.com/ |
| Oncogene Research Products | http://www.oncresprod.com/ |
| Open Biosystems | http://www.openbiosystems.com/ |
| Orbigen | http://www.orbigen.com/ |
| Oxford Biotechnology | http://www.oxfordbiotechnology.com/ |
| Pacific Immunology | http://www.pacificimmunology.com/ |
| Pall Corporation | http://www.pall.com/ |
| Panvera | http://www.panvera.com/ |
| PBL Biomedical Laboratories | http://www.interferonsource.com/ |
| Peprotech, Inc. | http://www.peprotechec.com/ |
| PerkinElmer Life Sciences | http://las.perkinelmer.com/ |
| Perseus Proteomics | http://www.ppmx.com/ |
| Pharmingen | http://www.pharmingen.com/ |
| Phoenix Pharmaceuticals | http://www.phoenixpeptide.com/ |
| PickCell Laboratories | http://www.pickcell.com/ |
| Pierce Chemical Company | http://www.piercenet.com/ |
| PlasmaLab International, Inc. | http://www.plasmalab.com/ |
| Polymun Scientific | http://www.polymun.com/ |
| Polysciences, Inc. | http://www.polysciences.com/ |
| PRF&L | http://www.prfal.com/ |
| Pro-Chem | http://www.protein-chem.com/ |
| Progen | http://www.progen.de/ |
| Promab Biotechnologies | http://www.promab.com/ |
| Promega Corporation | http://www.promega.com/ |
| ProSci | http://www.prosci-inc.com/ |
| Proteogenix | http://www.proteogenix.fr/ |
| Protos Immunoresearch | http://www.protosimmuno.com/ |
| QED Biosciences, Inc. | http://www.qedbio.com/ |
| Quidel Corporation | http://www.quidel.com/ |
| R&D Systems | http://www.rndsystems.com/ |
| Randox | http://www.randox.com/ |
| Repligen | http://www.repligen.com/ |
| Research Diagnostics | http://www.researchd.com/absort1.htm |
| Roboscreen | http://www.roboscreen.com/ |
| Rockland Immunochemicals | http://www.rockland-inc.com/ |
| Rose Biotech | http://www.rosebiotech.com/ |
| Santa Cruz Biotechnology | http://www.scbt.com/ |
| SCIpac | http://www.scipac.com/ |
| Scottish Agricultural Science | http://www.sasa.gov.uk/about_sasa/antibodies/index.cfm |
| ScyTek Laboratories | http://www.scytek.com/ |
| Seikagaku America | http://www.acciusa.com/ |
| Seramon | http://www.seramon.com/ |
| Serological Corporation | http://www.serologicals.com/ |
| Serotec | http://www.serotec.co.uk/ |
| SigmaAldrich | http://www.sigmaaldrich.com/ |
| Signature Immunologies | http://www.immunologics.com/ |
| Signet Laboratories | http://www.signetlabs.com/ |
| Silver Lake Research | http://www.silverlakeresearch.com/ |
| Southern Biotechnology Associates | http://www.southernbiotech.com/ |
| SPI-BIO | http://www.spibio.com/ |
| Statens Serum Institut | http://www.ssi.dk/antibodies |
| StemCell Technologies | http://www.stemcell.com/ |
| Sterogene Bioseparations | http://www.sterogene.com/ |
| Strategic Biosolutions | http://www.strategicbiosolutions.com/ |
| Stressgen | http://www.stressgen.com/ |

TABLE 1-continued

Immunoreagent Vendors

| Company | Website |
| --- | --- |
| Structure Probe, Inc. (SPI) | http://www.2spi.com/ |
| SWant | http://www.swant.com/ |
| Synaptic Systems GmbH | http://www.sysy.com/ |
| SynthOrg Biochemicals, Ltd. | http://synthorg.euro.ru/ |
| Technopharm | http://www.iphtec.com/ |
| Terra Nova Biotechnology | http://www.mun.ca/seabright/tnb/ |
| Tetra Link International | http://www.tetra-link.com/ |
| The Biotech Source | http://www.thebiotechsource.com/ |
| TiterMax | http://www.titermax.com/ |
| Transmissible Spongiform Encephalopothy Research Center | http://www.iah.bbsrc.ac.uk/tse-rc/ |
| Trevigen | http://www.trevigen.com/ |
| Trillium Diagnostics | http://www.trilliumdx.com/ |
| Triple Point Biologics | http://www.triplepointbiologics.com/ |

Develop Immunoassays: Immunoassays are preferably developed in three steps, Prototyping, Validation, and Kit Release.

Prototyping: Prototyping may be done using standard ELISA formats if the two antibodies used in the assay are from different host species. Using standard conditions, anti-host secondary antibodies conjugated with horse radish peroxidase are evaluated in a standard curve. If a good standard curve is detected, the assay proceeds to the next step. Assays that have same host antibodies go directly to the next step (i.e., mouse monoclonal sandwich assays).

Validation: Validation of a working assay may be performed using single molecule detection technology. The detection antibody is first conjugated to fluorescent molecules, typically Alexa 647. The conjugations use standard NHS ester chemistry, for example, according to the manufacturer. Once the antibody is labeled, the assay is tested in a sandwich assay format using standard conditions. Each assay well is solubilized in a denaturing buffer, and the material read on the single molecule detection platform.

FIG. 2 shows a typical result for a working standard curve. Once a working standard curve is demonstrated, the assay may be applied to 24 serum samples (for example) to determine the normal distribution of the target analyte across clinical samples. The amount of serum required to measure the biomarker within the linear dynamic range of the assay is determined, and the assay proceeds to kit release. In the present example, based on 39 validated assays, 0.004 microliters are used per well on average.

Kit Release: Each component of the kit including manufacturer, catalog numbers, lot numbers, stock and working concentrations, standard curve, and serum requirements may be compiled into a standard operating procedures for each biomarker assay. This kit may then be released for use in testing clinical research samples.

Acquiring Clinical Samples: Depending on the specification of the diagnostic test being developed, the clinical samples preferably have (for example) clinical annotations that track progression of disease, and preferably also include measurements of underlying mechanisms or disease phenotypes, and/or have disease outcomes using longitudinal samples over time. Relationships with the investigators may then be developed, and a contractual agreement is put into place. For each clinical study, the typical volumes range from 0.1 to 1 mL.

Import Clinical Annotations: Samples arrive frozen on dry ice, and each sample is stored at −80 C. Each sample typically has tens to hundreds of clinical annotations associated with it. The clinical annotations associated with each sample set may be brought into a standardized nomenclature prior to import. All of the clinical annotations associated with each sample are then imported into a relational database.

Prepare Clinical Samples: The frozen aliquots are thawed and aliquoted for use in the laboratory. Each clinical sample is thawed on ice, and aliquots are dispensed into barcoded tubes (daughter tubes). Each daughter tube is stored at −80 C until it is needed for immunoassays. The daughter tubes are then arrayed into sample plates. Each barcoded daughter tube to be assayed is arrayed into barcoded 96 or 384 well plates (sample plates). This daughter tube to sample plate well mapping is tracked by the relational database.

Run Immunoassays: Each sample plate is now prepared for immunoassays. In one example, 384 well barcoded assay plates may be dedicated to one biomarker per plate. Typically, 4-12 assay plates are derived from each sample plate dependent on the amount of serum required for each assay. The sample plate goes through a series of dilutions to ensure that the clinical samples are at an appropriate dilution for each immunoassay. The clinical samples are then deposited into the assay plate wells in triplicate for each marker. Again, tracking of each sample plate well to assay plate well is tracked in the relational database. The assays may then be processed using standard immunoassay procedures, and the assay plate is read on a single molecule detection instrument. Each run contains data for a single biomarker across multiple clinical samples, typically around one hundred. The resulting data files may then be imported back into the relational database, where standard curves can be calculated and the concentration values for each biomarker for each sample can be calculated. FIG. 3 shows an example of single molecule detection data across 92 samples for 25 biomarkers.

Analyze Data: The quantitative biomarker data can now be correlated to the clinical annotations associated with each sample. Any number of statistical formula or machine learning approaches on single or multiple markers can be used to identify disease states or risk for disease or biomarker patterns that have commercial potential to diagnose or prognose disease state (for example).

The following is an illustrative example of a Standard Operating Procedure (SOP) for use in developing diagnostic tests in accordance with an embodiment of the present invention.

Assay Analyte: C-Reactive Protein
Components:

| Component | Vendor | Catalog Number | Lot Number |
|---|---|---|---|
| C-Reactive Protein | US Biologicals | C7907-26A | L5042910 |
| Capture Antibody | US Biologicals | C7907-09 | L4030562 |
| Detection Antibody | US Biologicals | C7907-10 | L2121306M |

1. Plate Coating: Coat and block immunoassay plates for analyte capture
   1.1. Materials
      1.1.1. NUNC Maxisorp 384 well plates, Cat. No. 460518
      1.1.2. NUNC Acetate Sealers, Cat. No. 235306
      1.1.3. Coating buffer
         1.1.3.1. 0.05 M carbonate, pH 9.6
         1.1.3.2. Store at 4° C. for up to 2 months
      1.1.4. Capture Antibody
      1.1.5. Wash buffer A
         1.1.5.1. PBS with 0.1% Tween20
         1.1.5.2. Store at room temperature for up to 2 months
      1.1.6. Blocking Buffer
         1.1.6.1. 1% BSA, 5% sucrose, 0.05% $NaN_3$ in PBS
         1.1.6.2. Store at 4° C. for up to 1 month
      1.1.7. Microplate Washer
   1.2. Procedure
      1.2.1. Dilute capture antibody to 1 microgram/mL in coating buffer. (Prepare immediately before use)
      1.2.2. Add 20 microliters of diluted capture antibody per well
      1.2.3. Seal and shake for 2 minutes on plate shaker
      1.2.4. Centrifuge 1000 rpm 2 min, 25° C.
      1.2.5. Incubate overnight at room temperature (no shaking)
      1.2.6. Wash 3× with 100 microliters wash buffer A
      1.2.7. Add 30 microliters blocking buffer per well
      1.2.8. Seal and shake for 2 minutes on Jitterbug setting 7
      1.2.9. Centrifuge 1000 rpm 2 min, 25° C.
      1.2.10. Incubate at least 2 hour at room temperature (no shaking)
      1.2.11. Dump plate and blot upside down (no wash)
      1.2.12. Air dry the blocked plates (uncovered) at least 5 hours at room temperature
      1.2.13. Cover the dry plates with acetate sealer
      1.2.14. Store at 4° C. for up to one month
2. Single Molecule Detection Assay: Add clinical samples to coated plates and quantify
   2.1. Materials
      2.1.1. Coated, blocked NUNC Maxisorp 384 well plate
      2.1.2. NUNC Acetate Sealers, Cat. No. 235306
      2.1.3. Assay buffer
         2.1.3.1. BS* with 1% BSA, 0.1% TritonX-100.
         2.1.3.2. Store 4° C. for up to 1 month
      2.1.4. Standard Calibrator diluent
         2.1.4.1. Assay buffer+additional 5% BSA,
         2.1.4.2. Enough volume for standard curve, including 0 pg/ml.
         2.1.4.3. Make fresh for use.
      2.1.5. Standard Molecule Control
      2.1.6. Detection Antibody: A647 labeled antibody
      2.1.7. Assay Wash buffer B
         2.1.7.1. BS* with 0.02% Triton X-100 and 0.001% BSA
         2.1.7.2. 500 ml per assay plate
         2.1.7.3. Store at 4° C. for up to 1 month
      2.1.8. Elution Buffer
         2.1.8.1. 4 M urea, 1× BS with 0.02% Triton X-100 and 0.001% BSA
         2.1.8.2. Approx 8 ml per assay plate
      2.1.9. Microplate shaker (Jitterbug), set at "7"
      2.1.10. Microplate washer
      2.1.11. Centrifuge
   2.2. Procedure
   2.3. Record
      2.3.1. Plate assay plate number, kit lot number, and sample plates used
   2.4. Standard Curve
      2.4.1. Dilute control to 100 ng/ml in calibrator
      2.4.2. Prepare ½ serial dilutions from 100 ng/ml to 0.01 pg/ml in calibrator diluent
   2.5. Sample Dilution
      2.5.1. Dilute samples 1:400 in assay buffer
   2.6. Capture and Detection
      2.6.1. Add 20 microliters/well of standards
      2.6.2. Add 20 microliters/well diluted unknowns
      2.6.3. Seal w/acetate sealing tape. Shake for 2 minutes on plate shaker
      2.6.4. Incubate overnight at room temperature
      2.6.5. Dilute Detection antibody labeled A647 antibody to 50 ng/ml in assay buffer.
      2.6.6. Aspirate. Wash 5× with 100 ul wash buffer B
      2.6.7. Blot Upside Down
      2.6.8. Add 20 microliters/well diluted detection antibody
      2.6.9. Seal w/acetate sealing tape. Shake for 2 minutes on plate shaker
      2.6.10. Incubate 2 hours at room temperature
      2.6.11. Aspirate. Wash 5× with 100 ul wash buffer B
      2.6.12. Blot Upside Down
      2.6.13. Add 20 microliters/well elution buffer.
      2.6.14. Seal w/acetate sealing tape. Shake for 2 minutes on plate shaker.
      2.6.15. Incubate ½ hour at 25° C.
      2.6.16. Centrifuge on 1000 rpm for 2 min, 25° C.
   2.7. Analyze on Single Molecule Detection instrument Other Embodiments It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. In a method of evaluating the health state of a live subject, comprising obtaining a measurement of at least one clinical biomarker from at least one live clinical sample isolated from said live subject, and inputting said measurement(s) into a model that calculates an output value correlated to said health state, the improvement comprising using as said model an algorithm that was developed by measurement of multiple development biomarkers comprising said clinical biomarker(s) from at least one legacy clinical sample set annotated for said health state, said measurement comprising use of legacy clinical samples having a sample volume of 1 ml or less, and analyzing said measurement of multiple biomarkers for an association with said health state.

2. The method of claim 1, wherein said measurement of multiple development biomarkers comprises measuring at least two biomarkers from said sample volume.

3. The method of claim 2, wherein said measurement of multiple development biomarkers comprises measuring at least 10 biomarkers from a sample volume less than about 0.5 milliliters.

4. The method of claim 2, wherein said measurement of multiple development biomarkers comprises measuring at least 20 biomarkers from said sample volume.

5. The method of claim 2, wherein said measurement of multiple development biomarkers comprises measuring at least 100 biomarkers from said sample volume.

6. The method of claim 2, wherein said measurement of multiple development biomarkers comprises measuring at least 200 biomarkers from said sample volume.

7. The method of claim 2, wherein said measurement of multiple development biomarkers comprises measuring at least 300 biomarkers from said sample volume.

8. The method of claim 1, wherein said measurement of multiple development biomarkers comprises, for each biomarker, measuring said biomarker in an assay of said legacy clinical sample, wherein said assay used about 1 microliter (uL) or less of said sample volume for each biomarker.

9. The method of claim 8, wherein at least 10 development biomarkers are measured per legacy clinical sample.

10. The method of claim 8, wherein said measurement of multiple development biomarkers used single molecule detection to measure said multiple development biomarkers in said legacy clinical sample.

11. The method of claim 1, wherein said health state is the presence or absence of a disease.

12. The method of claim 1, wherein said health state is pre-disease or a pre-disease condition.

13. The method of claim 1, wherein said health state is the risk of developing a disease.

14. The method of claim 11, wherein said absence of a health state is further defined to be a normal state or pre-disease state.

15. The method of claim 1, wherein said biomarkers comprise traditional laboratory risk factors.

* * * * *